United States Patent
Keren

(10) Patent No.: US 6,754,522 B2
(45) Date of Patent: Jun. 22, 2004

(54) IMAGING METHODS AND APPARATUS PARTICULARLY USEFUL FOR TWO AND THREE-DIMENSIONAL ANGIOGRAPHY

(75) Inventor: Hanan Keren, Kfar Saba (IL)

(73) Assignee: MediMag C.V.I., Inc., Wilmington, DE (US)

(*) Notice: Subject to any disclaimer, the term of this patent is extended or adjusted under 35 U.S.C. 154(b) by 53 days.

(21) Appl. No.: 10/144,007

(22) Filed: May 14, 2002

(65) Prior Publication Data

US 2003/0048935 A1 Mar. 13, 2003

Related U.S. Application Data

(63) Continuation-in-part of application No. 09/946,168, filed on Sep. 5, 2001, now Pat. No. 6,574,500.

(51) Int. Cl.[7] .................................................. A61B 6/00
(52) U.S. Cl. ...................... 600/431; 600/425; 378/98.11; 382/130
(58) Field of Search ................................. 600/407, 420, 600/425, 431, 458; 378/98.11, 51; 382/130

(56) References Cited

U.S. PATENT DOCUMENTS

| | | | |
|---|---|---|---|
| 5,125,018 A | 6/1992 | Asahina | |
| 5,408,521 A | 4/1995 | Grady | |
| 5,602,891 A | 2/1997 | Pearlman | |
| 5,630,414 A | 5/1997 | Horbaschek | |
| 5,647,360 A | 7/1997 | Bani-Hashemi et al. | |
| 5,690,106 A | 11/1997 | Bani-Hashemi et al. | |
| 5,743,266 A | 4/1998 | Levene et al. | |
| 5,801,385 A | 9/1998 | Endo et al. | |
| 5,802,133 A | 9/1998 | Kawai et al. | |
| 5,839,440 A | 11/1998 | Liou et al. | |
| 5,841,830 A | 11/1998 | Barni et al. | |
| 5,852,646 A | 12/1998 | Klotz et al. | |
| 5,978,439 A | 11/1999 | Koppe et al. | |
| 5,982,845 A | 11/1999 | Sidoti et al. | |
| 6,041,097 A | 3/2000 | Roos et al. | |
| 6,047,080 A | 4/2000 | Chen et al. | |
| 6,052,476 A | 4/2000 | Qian et al. | |
| 6,075,836 A | 6/2000 | Ning | |
| 6,113,264 A | 9/2000 | Watanabe | |
| 6,118,845 A | 9/2000 | Simon et al. | |
| 6,154,516 A | 11/2000 | Heuscher et al. | |
| 6,574,500 B2 * | 6/2003 | Keren | ........................ 600/431 |

* cited by examiner

Primary Examiner—Ruth S. Smith
(74) Attorney, Agent, or Firm—G.E Ehrlich (1995) Ltd.

(57) ABSTRACT

A method and apparatus for angiographically imaging a portion of a patient's vascular system, by:

(a) producing a first sequence of masking images of the portion of the patient's vascular system;

(b) determining the masking image in the sequence having a minimum change over its immediately preceding masking image in the sequence;

(c) injecting a contrast material into the patient's vascular system;

(d) producing a corresponding sequence of contrast images of the portion of the patient's vascular system while containing the contrast material and (e) subtracting from each contrast image of the sequence the corresponding masking image in the sequence starting with the minimum change masking image, to thereby produce a difference image having an enhanced contrast-to-noise ratio (CNR).

18 Claims, 7 Drawing Sheets

IMAGING METHODS AND APPARATUS PARTICULARLY USEFUL FOR TWO AND THREE-DIMENSIONAL ANGIOGRAPHY

RELATED APPLICATION

The present application is a continuation-in-part of my prior U.S. application Ser. No. 09/946,168, filed Sep. 5, 2001, now U.S. Pat. No. 6,574,500, the total contents of which are incorporated herein by reference.

FIELD AND BACKGROUND OF THE INVENTION

The present invention relates to methods and apparatus for imaging two-dimensional (2-D) planes or surfaces and/or three-dimensional (3-D) objects. The invention is particularly useful in angiography for imaging a person's vascular system in 2-D or 3-D, and is therefore described below with respect to this application.

Electromagnetic radiation has long been used to produce images of internal structures of the human body for purposes of diagnosis or treatment of diseases. One technique which has gained widespread use since the 1970's is computerized tomography (CT), sometimes called computerized axial tomography (CAT), in which a narrow beam of X-rays is swept across an area of the body and is recorded by a radiation detector as a pattern of electrical impulses, while a computer is used to integrate the data for many such sweeps and to reconstruct a two-dimensional or a three-dimensional image of the examined volume. In the current CT systems, the radiation source generally produces a fan-shaped beam, and the radiation detector generally includes a line of detector elements aligned with the fan-shaped beam so as to detect the level of the radiation after having traversed the object being examined.

When a 3-D image is to be produced, the body is exposed to the radiation at a plurality of different image planes (slices), each at a different angular position, while a large number of gray levels of radiation are sensed by each detector element. For example, a typical procedure may involve in the order of 256 slices, each at 128 different angular positions, with each detector element recording up to 128, 256, 512 or 1024 gray levels. Many reconstruction algorithms are known for reconstructing the three-dimensional image from this data.

Angiography, on the other hand, involves the radiographic examination of arteries and veins, in which a contrast medium is injected into the vascular system to cause a denser shadow than would be caused by other tissues, thereby enabling the blood vessels to be distinguished from the other tissues. In digital subtraction angiography (DSA), an X-ray image (called a "masking image") of the patient is taken before the contrast material is injected; and another X-ray image (called a "contrast image") is taken after the contrast material is injected. The masking image is subtracted from the contrast image to leave only the DSA image of the blood vessels, enabling them to be readily distinguished from the other tissue.

According to the prior art, angiographically imaging a portion of a patient's vascular system thus involves: producing a first sequence of masking images of the portion of the patient's vascular system; injecting a contrast material into the patient's vascular system; producing a corresponding sequence of contrast images of the portion of the patient's vascular system while containing the contrast material and subtracting from each contrast image of the sequence the corresponding masking image in the sequence to thereby produce a difference image having an enhanced contrast-to-noise ratio (CNR).

Examples of known DSA systems are described in U.S. Pat. Nos. 5,630,414, 6,052,476, 6,075,836 and 6,118,845, the disclosures of which are incorporated herein by reference.

Such a subtraction process was generally performed, according to the prior art, by using an ECG sensor or a respiration sensor as the reference point for the subtraction process. However, using a respiration sensor as the reference is not precise because of the difficulty in sharply defining a particular point of the respiration curve for this purpose. Similarly, utilizing an ECG sensor is also not precise for the same reason. Moreover, the mere presence of an ECG sensor can effect the ECG signal detected from the patient's body.

The value of the images produced by DSA for diagnostic or treatment purposes depends to a high degree on the contrast-to-noise ratio (CNR) of the DSA image. The CNR of an image is to be distinguished from the signal-to-noise ratio (SNR), and is generally defined as being the difference in the SNRs of adjacent imaged regions. Thus, enhancing the CNR of a DSA image would better enable the physician to discern details of the patient's vascular system and therefore better enable the physician to utilize this information for diagnostic or treatment purposes.

OBJECTS AND BRIEF SUMMARY OF THE INVENTION

An object of the present invention is to provide an improved method and apparatus for producing two-dimensional or three-dimensional angiographic images to better enable diagnosis or treatment of a disease in the human body. A further object of the invention is to provide a method and apparatus for enhancing the CNR of a DSA image.

According to one aspect of the present invention, there is provided a method of angiographically imaging a portion of a patient's vascular system, comprising the steps:

(a) producing a first sequence of masking images of the portion of the patient's vascular system;

(b) determining the masking image in the sequence having a minimum change over its immediately preceding masking image in the sequence;

(c) injecting a contrast material into the patient's vascular system;

(d) producing a corresponding sequence of contrast images of the portion of the patient's vascular system while containing the contrast material and (e) subtracting from each contrast image of the sequence the corresponding masking image in the sequence, starting with the minimum change masking image, to thereby produce a difference image having an enhanced contrast-to-noise ratio (CNR).

It has been found that using the masking image of minimum change as a reference for the digital subtraction operation, instead of an ECG signal or respiration signal, not only obviates the need for an ECG sensor or respiration sensor but, even more importantly, produces a DSA having an enhanced CNR as compared to previous techniques using such sensors. Thus, using the masking image of minimum change as a reference permits more precise time-correlation of the masking images to be subtracted from the corresponding contrast images. Moreover, this technique does not require a special sensor, such as an ECG sensor, which might affect the sensor signal merely because of the presence of the sensor.

According to a further feature in the described preferred embodiment, in the subtraction step, the respective contrast image is multiplied by a factor (k) of 1 to 3 before the corresponding masking image is subtracted therefrom. Preferably, the factor (k) is 1.8. That is, if each masking image in the first sequence (before injection) is subtracted from 1.8 times the corresponding contrast image, starting with the minimum change masking image, a substantial enhancement of the resulting difference image is obtained.

In step (b) of the preferred embodiments described below, a pixel-by-pixel comparison of the gray-level of the pixels in the respective masking image is made with the corresponding pixels in the preceding masking image of the sequence, and the masking image of the sequence having minimum changes over its immediately preceding masking image in the sequence is selected as the masking image of minimum change.

In step (e) of one described preferred embodiment, there is subtracted from each contrast image of the contrast image sequence, the gray-levels of the corresponding masking image in the masking image sequence, starting with the minimum change masking image, to thereby produce a difference image having an enhanced contrast-to-noise ratio (CNR). In step (e) of a second described embodiment, there is subtracted from each contrast image of the contrast image sequence, the gray-levels of the corresponding masking image in the masking image sequence, averaged with the gray-levels of the next masking image in the masking image sequences starting with the minimum change masking image, to thereby produce a difference image having an enhanced contrast-to-noise ratio (CNR). This averaging technique tends to average-out errors in the time-correlation during the subtraction step, and thereby, in many cases, produces a further enhancement of the resulting difference image.

In step (e) of both described embodiments, a pixel-by-pixel comparison of the gray-level of each pixel in the respective contrast image is made with the corresponding pixel in the preceding contrast image of the sequence. The contrast image of the sequence having minimum changes over its immediately preceding contrast image in the sequence is used as the starting point, together with the minimum change masking image, for subtracting from each contrast image the corresponding masking image.

According to still further features in another described preferred embodiment, the first sequence of masking images and the corresponding sequence of contrast images are produced by a radiation source and a radiation detector located on opposite sides of the patient; relative linear movement is effected between the patient and the radiation source and radiation detector during the two image sequences; and a linear positional transformation is performed to normalize each of the images with respect to the relative movement before the masking images are subtracted from the contrast images to produce the difference images having an enhanced CNR.

The linear positional transformation in the described preferred embodiment is performed by measuring the relative change in position of the patient with respect to the radiation source and radiation detector when producing the two sequences of images; measuring the gray-level in each of the pixel positions in each of the masking images and contrast images; and modifying the pixel positions in each of the masking images and contrast images according to the measured relative change in the position of the patient for the respective masking image and contrast image.

The latter feature enables a larger number of the images to be used, and/or a larger region to be examined, in producing the two-dimensional angiograms of enhanced CNR, since it allows use of the angiograms produced while relative movement is effected between the patient and the radiation source and radiation detector, as well as those in which the patient is non-moving.

According to another feature in a described preferred embodiment, the radiation source and radiation detector are carried on a gantry which is rotated around the patient to a plurality of angular positions to produce a sequence of the masking images and the contrast images for each angular position; and a difference image having an enhanced CNR is produced for each of the angular positions. The difference images for the plurality of angular positions may then be reconstructed to produce a 3-D image of enhanced CNR according to presently-known techniques.

According to another aspect of the present invention, there is provided apparatus producing angiographical images of a portion of a patient's vascular system, comprising: a radiation source to be located at one side of the patient for radiating the portion of the patient's vascular system; a radiation detector to be located at the opposite side of the patient for producing electrical outputs corresponding to the magnitude of the radiation received by the detector; a computer for controlling the radiation source and for processing the outputs of the radiation detector to produce an image of the portion of the patient's vascular system; and a display for displaying the produced image; the computer controlling the radiation source and processing the outputs of the radiation detector such that: before a contrast material is injected into the patient's vascular system and a sequence of masking images is produced of the portion of the patient's vascular system, a determination is made as to the masking image in the sequence having a minimum change over its immediately preceding masking image; and after a contrast material is injected into the patient's vascular system and a corresponding sequence of contrast images is produced, from each contrast image the corresponding masking image in the sequence is subtracted starting with the masking image determined to have a minimum change over its immediately preceding masking image, to thereby produce a difference image having an enhanced contrast-to-noise ratio (CNR) which is displayed in the display.

As will be described more particularly below, such method and apparatus can be used for both two-dimensional angiography as well as for three-dimensional angiography.

Further features and advantages of the invention will be apparent from the description below.

BRIEF DESCRIPTION OF THE DRAWINGS

The invention is herein described, by way of example only, with reference to the accompanying drawings, wherein.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF PREFERRED EMBODIMENTS

The Embodiment of FIGS. 1–6

Figure 1:
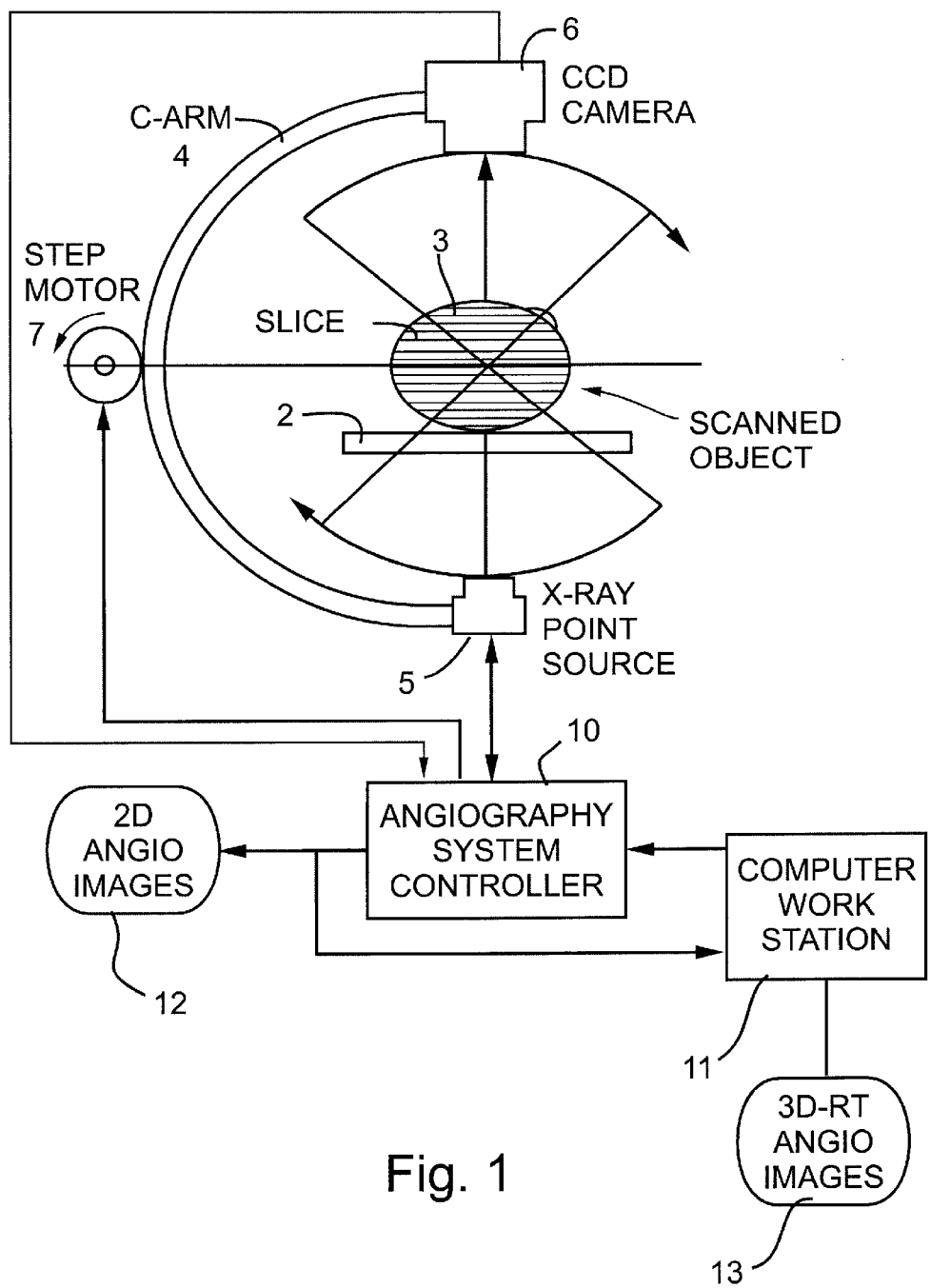
FIG. 1 is a block diagram illustrating one form of apparatus constructed in accordance with the present invention.

FIG. 1 schematically illustrates one form of apparatus constructed in accordance with the present invention particularly useful for producing either two-dimensional angiographs and/or three-dimensional angiographs of a patient's vascular system.

Figure 2:
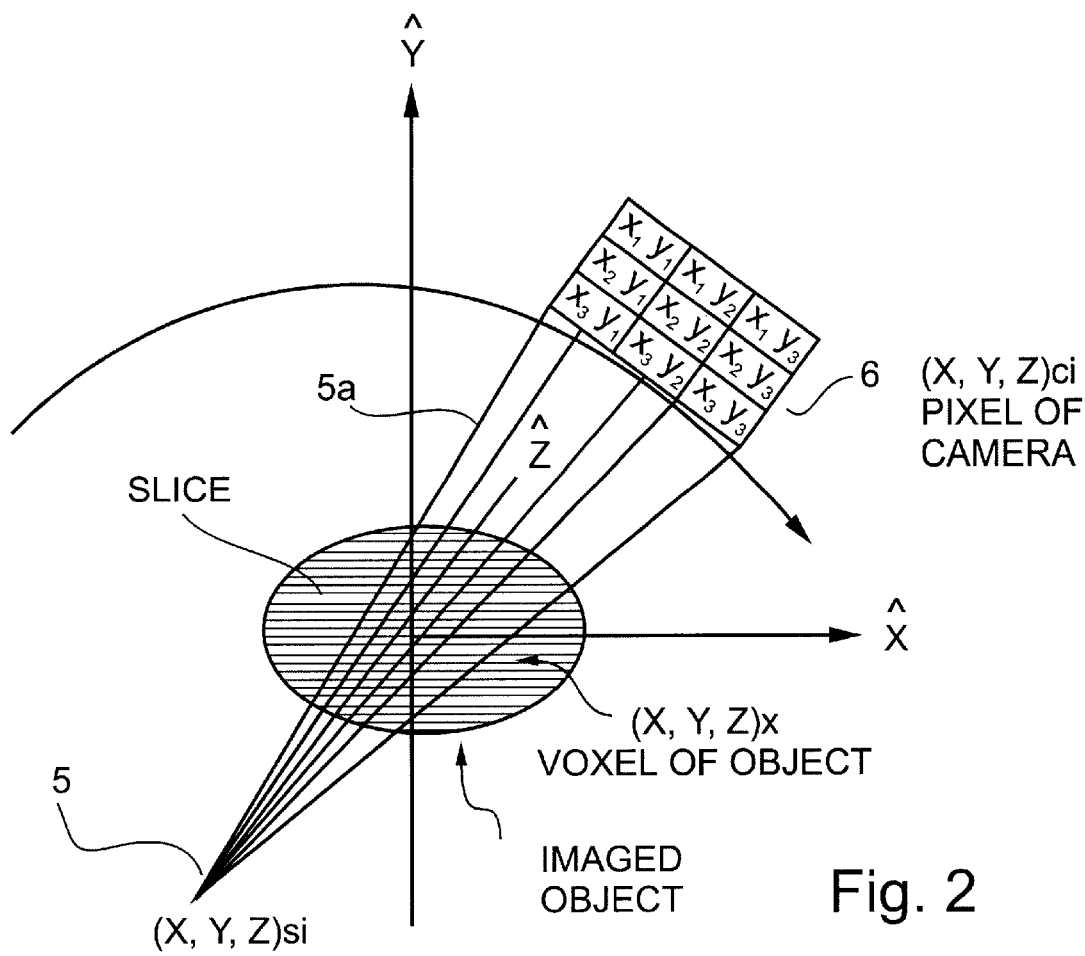
FIG. 2 is a diagram helpful in explaining the operation of the apparatus of FIG. 1.
Figure 4:
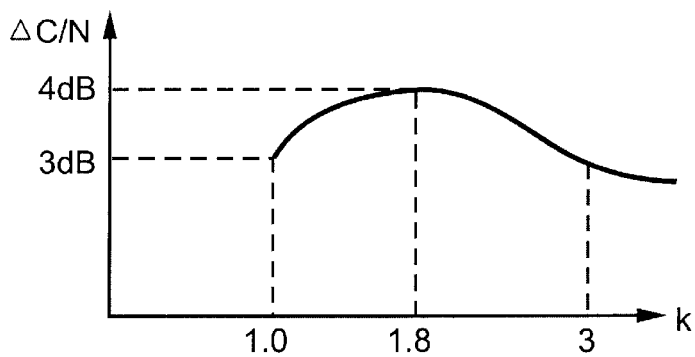
FIG. 4 is an emperical curve illustrating the enhancement of the contrast-to-noise ratio (CNR) produced by the subtraction technique of the apparatus of FIG. 1.

The system illustrated in FIG. 1 includes a horizontal support such as a table 2 for the patient 3 under examination, and a gantry C-arm 4, such as used in CT examination apparatus, enclosing the patient's body 3. The C-arm supports a radiation source 5 at one side of the patient's body, and a radiation detector 6 at the opposite side and in alignment with the radiation source. The radiation source 5 is an X-ray point source which produces a conical beam 5a as shown in FIG. 2; and the radiation detector 6, preferably a CCD camera, includes a two-dimensional matrix of detector elements as best seen in FIG. 4. As shown particularly in FIG. 2, the conical beam 5a produced by the radiation source 5 in each angular position is sufficiently large to cover all the detector elements in the two-dimensional matrix 6 after traversing the body 3 under examination.

The apparatus illustrated in FIG. 1 further includes a step motor 7 for changing the angular position of the radiation source 5 and radiation detector 6 with respect to the body 3 under examination. In the preferred embodiment of the invention described below, the step motor 7 is capable of rotating the radiation source 5 and the radiation detector 6 about the Z-axis, which is the longitudinal axis of the patient's body 3, and also about the X-axis, which defines with the Z-axis the plane of the horizontal body support 2.

The electronics in the apparatus illustrated in FIG. 1 includes an angiography system controller 10 which controls the radiation source 5 and also the step motor 7 to successively produce the exposures of the body 3 from a plurality of different angular positions with respect to the body. Controller 10 also receives the electronic outputs from the radiation detector elements in the CCD camera 6, and processes those outputs as will be described more particularly below.

The apparatus illustrated in FIG. 1 further includes a computer work station 11 which controls the angiography system controller 10 to produce a two-dimensional display of the angio images on a monitor 12 at the work station of any selected angio plane (or slice) in the volume under examination. The illustrated system includes a further monitor 13 which may be used for displaying a 3-D image of the volume under examination by reconstructing a plurality of the two-dimensional images.

FIG. 2 illustrates a simplified two-dimensional matrix of detector elements, showing only three horizontal rows (x) and three vertical columns (y). It will be appreciated that the CCD camera 6 would include a much larger number of detector elements, preferably a matrix of at least 128 by 128 detector elements, and more preferably a matrix of 256 by 256 or 512 by 512 detector elements. In the simplified illustration of FIG. 2, the three horizontal rows of detector elements are identified as $X_1$–$X_3$; and the three vertical columns are identified as $Y_1$–$Y_3$. Each detector element defines a pixel of the detected image and produces a measurement of the gray-level of the respective pixel, as well as identification of the position of the respective pixel.

The apparatus illustrated in FIG. 1 is used for producing a two-dimensional image or angiogram of a predetermined plane or slice of a patient's vascular system by digital subtraction aniography (DSA). As briefly described earlier, this involves producing a sequence of masking images of the respective plane of the patient's vascular system; injecting a contrast material into the patient's vascular system; producing a corresponding sequence of contrast images of the respective plane of the patient's vascular system while containing the contrast material; and subtracting, from each contrast image of the sequence, the corresponding masking image in the sequence to thereby produce a DSA image of the blood vessels enabling them to be distinguished from the other tissues.

In the conventional DSA system, the angiography system controller (10, FIG. 1) is generally controlled in synchronization with cardiac and/or respiratory gating signals produced by an ECG sensor or a respiration sensor (not shown). According to the present invention, however, the angiography system controller 10 is controlled in synchronization with the masking image having a minimum change over its immediately preceding masking image in the respective sequence. The masking image determined to have the least change over its immediately preceding masking image is thus used as the reference point for this subtraction process. Thus, after the contrast material has been injected, there is subtracted, from each contrast image of the after-injection sequence, the corresponding masking image in the before-injection sequence, starting with the masking image having minimum changes over its preceding masking image.

As indicated earlier, using the masking image of minimum change as a reference for the digital subtraction operation, not only obviates the need for an ECG sensor or respiration sensor, but has been found to produce a DSA having an enhanced CNR as compared to techniques using such sensors as a reference for the digital subtraction operation. Thus, using a respiration sensor signal and/or an ECG sensor signal, as a reference for the digital subtraction operation as known in the prior art, not only lacks precision because of the difficulty in identifying a particular point of the respiration and/or cardiac curve for this purpose; but also the mere presence of such a sensor, particularly an ECG sensor, may even affect the signal detected from the patient's body.

Figure 3:
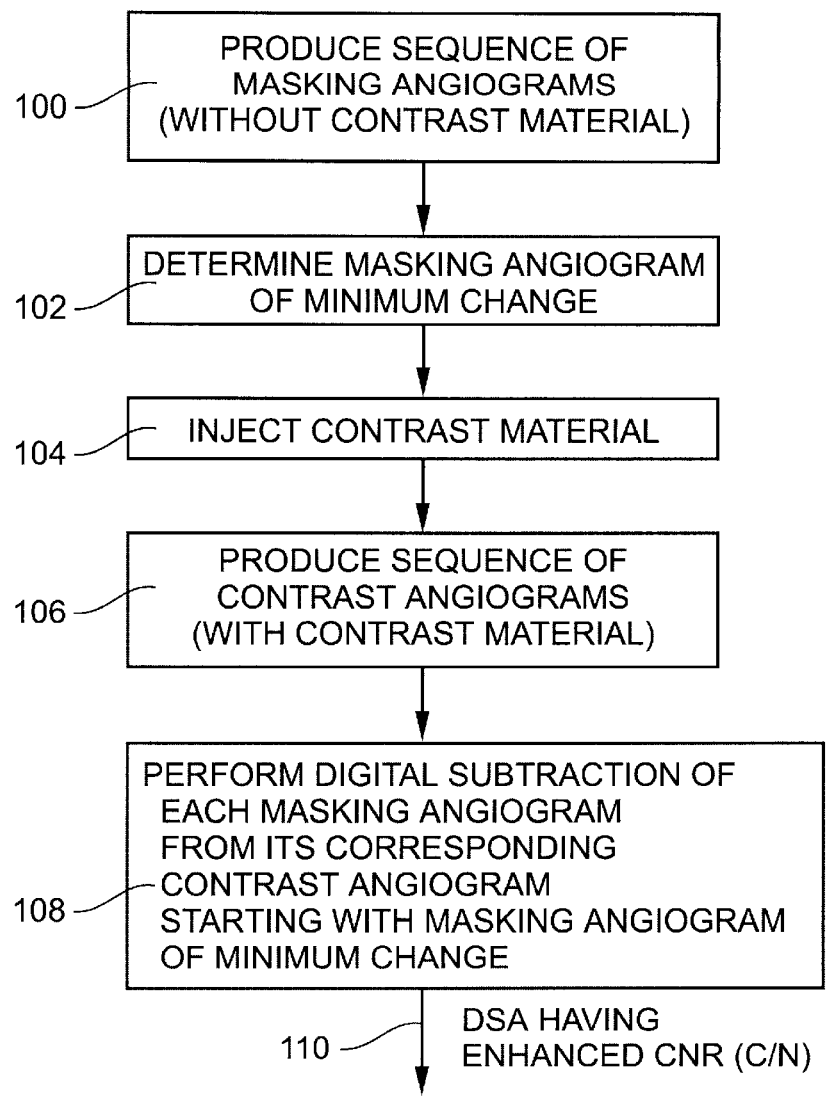
FIG. 3 is a flow chart illustrating the operation of the apparatus of FIG. 1.

FIG. 3 is a flow chart illustrating one manner of using the apparatus of FIG. 1 for producing DSA (digital subtracting angiograms) having an enhanced CNR (contrast-to-noise ratio) with respect to the portion of the patient's cardiovascular system examined by the apparatus.

Thus, as shown in the flow chart of FIG. 3, before a contrast material is injected into the patient, there is produced a sequence of masking angiograms (block 100); and a determination is made as to the masking angiogram having the minimum change over its immediately preceding angiogram (block 102).

The contrast material is then injected (block 104); and a corresponding sequence of contrast angiograms is now produced of the respective portion of the patient's vascular system (block 106).

The computer then performs a digital subtraction of each masking image from its corresponding contrast image, starting with the masking image determined to have the least change over its immediately preceding masking image (block 108). The masking image determined to have the least change over its immediately preceding masking image is thus used as the reference point for starting this subtraction process with respect to the corresponding contrast images starting at the corresponding point of that sequence, i.e., the contrast image having minimum changes over its immediately preceding contrast image. As indicated earlier it has been found that using the masking image of minimum change as a reference for the digital subtraction operation, produces a DSA having an enhanced CNR as compared to previous techniques.

FIG. 4 is an emperical curve illustrating how the foregoing subtraction technique enhances the contrast-to-noise ratio (CNR). Thus, as shown in FIG. 4, in the subtraction step wherein the matching images are subtracted from their respective contrast images, if the respective contrast image is first multiplied by a factor (k) of "1", there is an increase in the CNR of the resulting DSA of approximately 3 dB. That is, if the masking image is subtracted from the respective contrast image on a one-to-one basis, the enhancement of the CNR is approximately 3 dB.

FIG. 4, however, shows how this enhancement can be increased to about 4 dB, by changing the factor (k) to 1.8. That is, if the masking image is subtracted from 1.8 times the respective contrast image, the enhancement of the resulting difference signal is increased about 4 dB.

As shown in FIG. 4, the factor (k) is therefore preferably from 1–3, to produce an enhancement of between 3 dB to 4 dB, in the particular example illustrated in FIG. 13.

Figure 5:
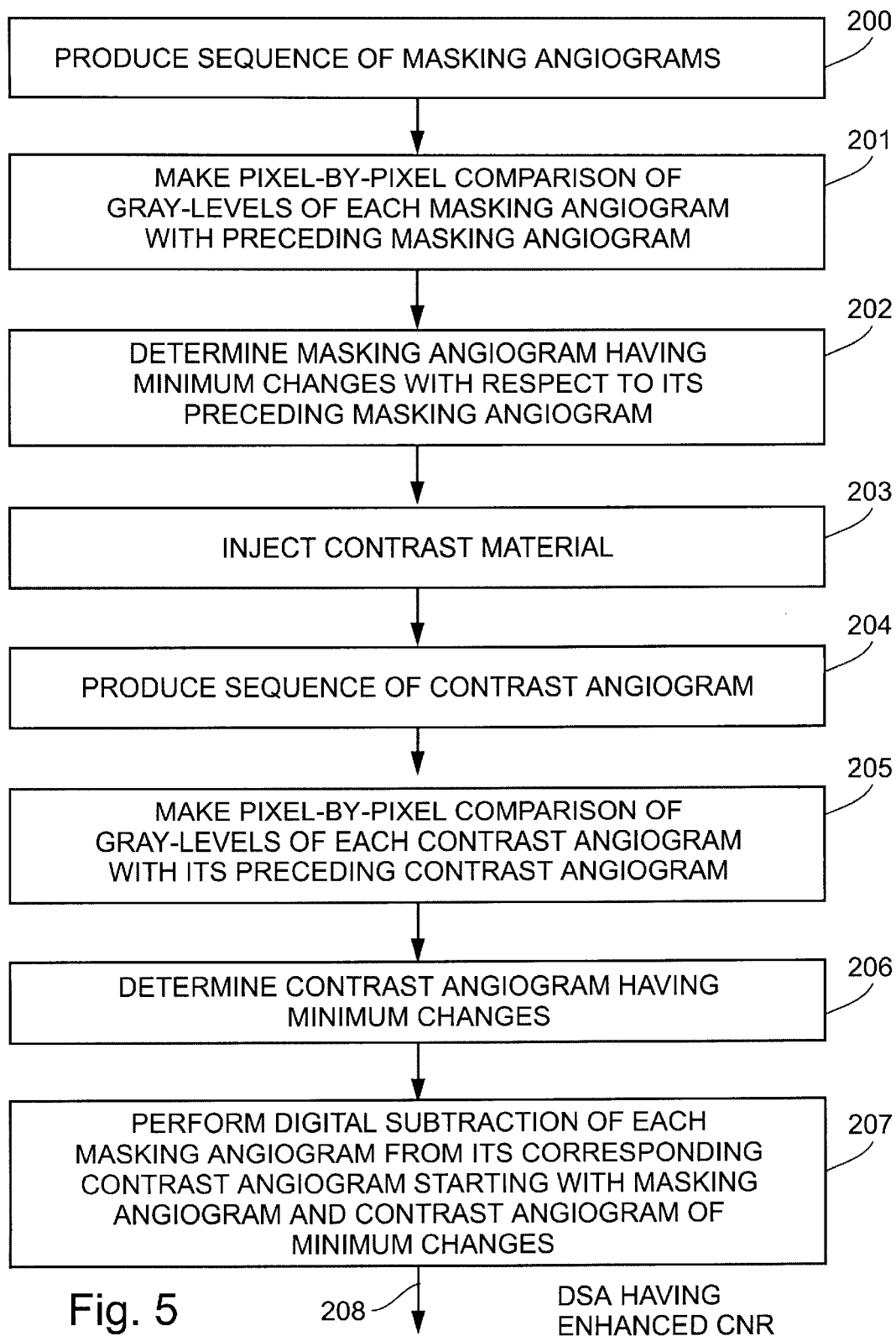
FIGS. 5 and 6 are two flow charts more particularly illustrating two modes of operation of the apparatus of FIG. 1.

FIG. 5 more particularly illustrates one manner of implementing the flow chart of FIG. 3, particularly in determining the masking angiogram of minimum change to be used as a starting point in the subtraction process. Thus, as shown in FIG. 5, a sequence of masking angiograms are produced (block 200); and a pixel-by-pixel comparison is made of the gray-levels of each masking angiogram with its immediately preceding masking angiogram (block 201). This may be done by comparing, on a pixel-by-pixel basis, the gray-level of each pixel in the masking image with respect to the pixels in the immediately preceding masking image of the sequence, and determining which masking image has the minimum change over its immediately preceding masking image. For example, the sequence of masking images could be for a period of the order of 2–4 seconds, so that there would be about 50–100 images or frames in the respective sequence. The computer work station 11 stores all this information from each masking image in the sequence, and also makes the determination as to the masking image having the least change over its immediately preceding one (block 202).

The contrast material is then injected (block 203); and a corresponding sequence of contrast angiograms is now produced of the respective portion of the patient's vascular system (block 204). To determine the point of the sequence of contrast images corresponding to the minimum-change masking image in the sequence of masking images, a pixel-by-pixel comparison is made of the gray-levels of each contrast angiogram with its preceding contrast angiogram (block 205); and a determination of the contrast angiogram having minimum changes with its preceding contrast angiogram is determined (block 206).

The computer then performs a digital subtraction of each masking image from its corresponding contrast image, starting with the masking image determined to have the least change over its immediately preceding masking image, and the contrast image having the least change over its immediately preceding contrast image, to produce a DSA having enhanced CNR (block 207).

Figure 6:
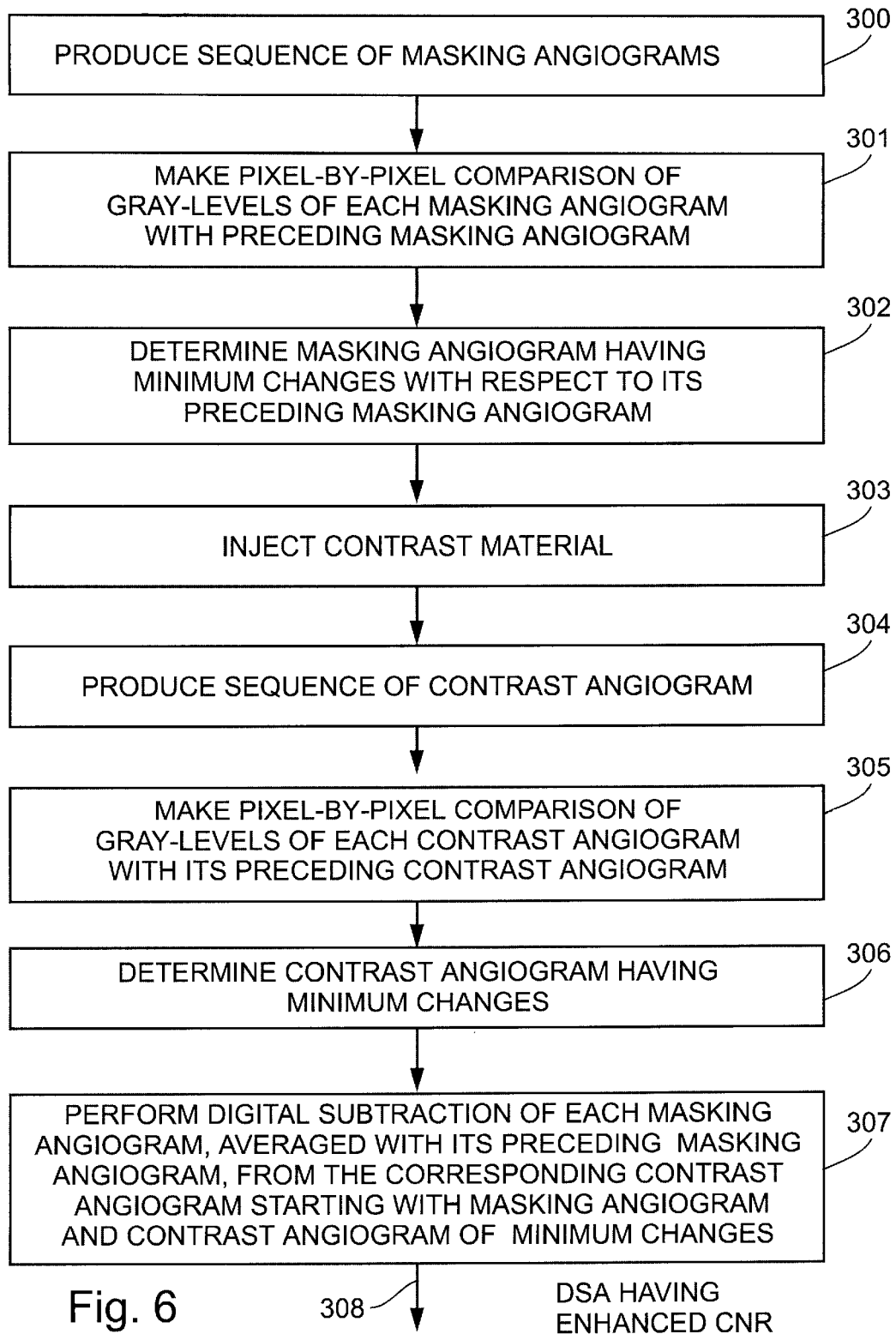

FIG. 6 is a block diagram illustrating a slightly different process. The process of FIG. 6 includes operations 300–306, which are the same as operations 200–206, respectively, in FIG. 5. Operation 307 of FIG. 6, however, is slightly different from operation 207 of FIG. 5, in that, in operation 307, the digital subtraction is effected of the average of each masking angiogram with its preceding masking angiogram.

That is, in the digital subtraction step of block 207 in FIG. 5, there is subtracted from each contrast image of the contrast image sequence, the gray-levels of the corresponding masking image in the masking image sequence, starting with the minimum change masking image, to thereby produce a difference image having an enhanced contrast-to-noise ratio (CNR).

On the other hand, in the digital subtraction step of block 307 in FIG. 6, there is subtracted from each contrast image of the contrast image sequence, the gray-levels of the corresponding masking image in the masking image sequence, averaged with the gray-levels of the next masking image in the masking image sequence, starting with the minimum change masking image, to thereby produce a difference image having an enhanced contrast-to-noise ratio (CNR).

It has been found that this averaging technique sometimes produces a better DSA having a more enhanced CNR. This is because of the difficulty in time-correlating the sequence of masking angiogram with the sequence of contrast angiograms. Thus, it tends to average-out errors in such a time-correlation.

In order to produce a 3-D angiogram, the C-arm gantry 4 is rotated around the patient to a plurality of angular positions, and a DSA image having an enhanced CNR is produced for each angular position. The DSA images for the plurality of angular positions are then reconstructed according to techniques known in the prior art such as those described in the above-cited prior U.S. Patents, to produce a 3-D image of enhanced CNR of the patient's vascular system.

Figure 7:
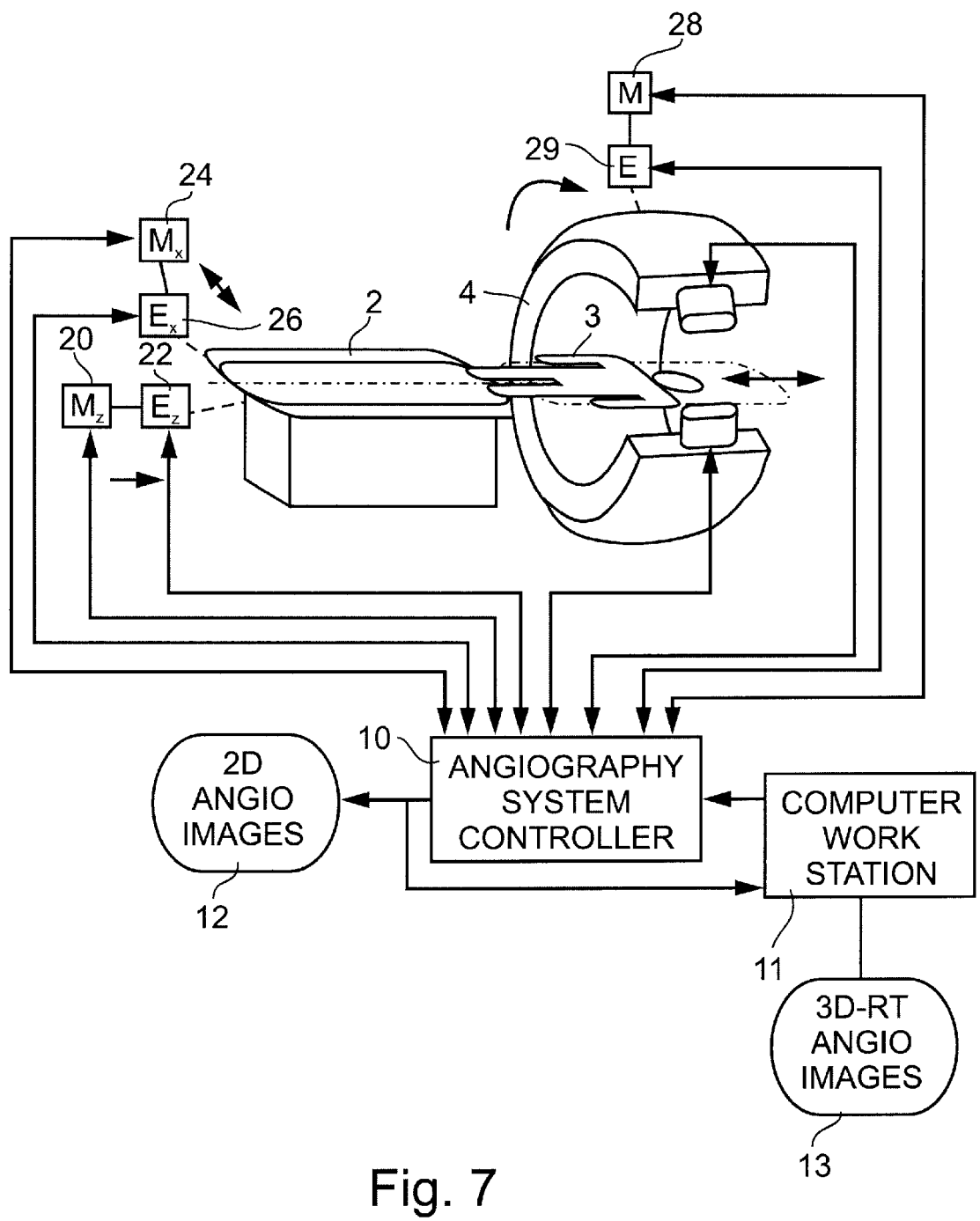
FIG. 7 is a block diagram illustrating another apparatus constructed in accordance with the present invention permitting linear movement of the table, and thereby of the patient thereon, with respect to the radiation source and radiation detector.
Figure 8:
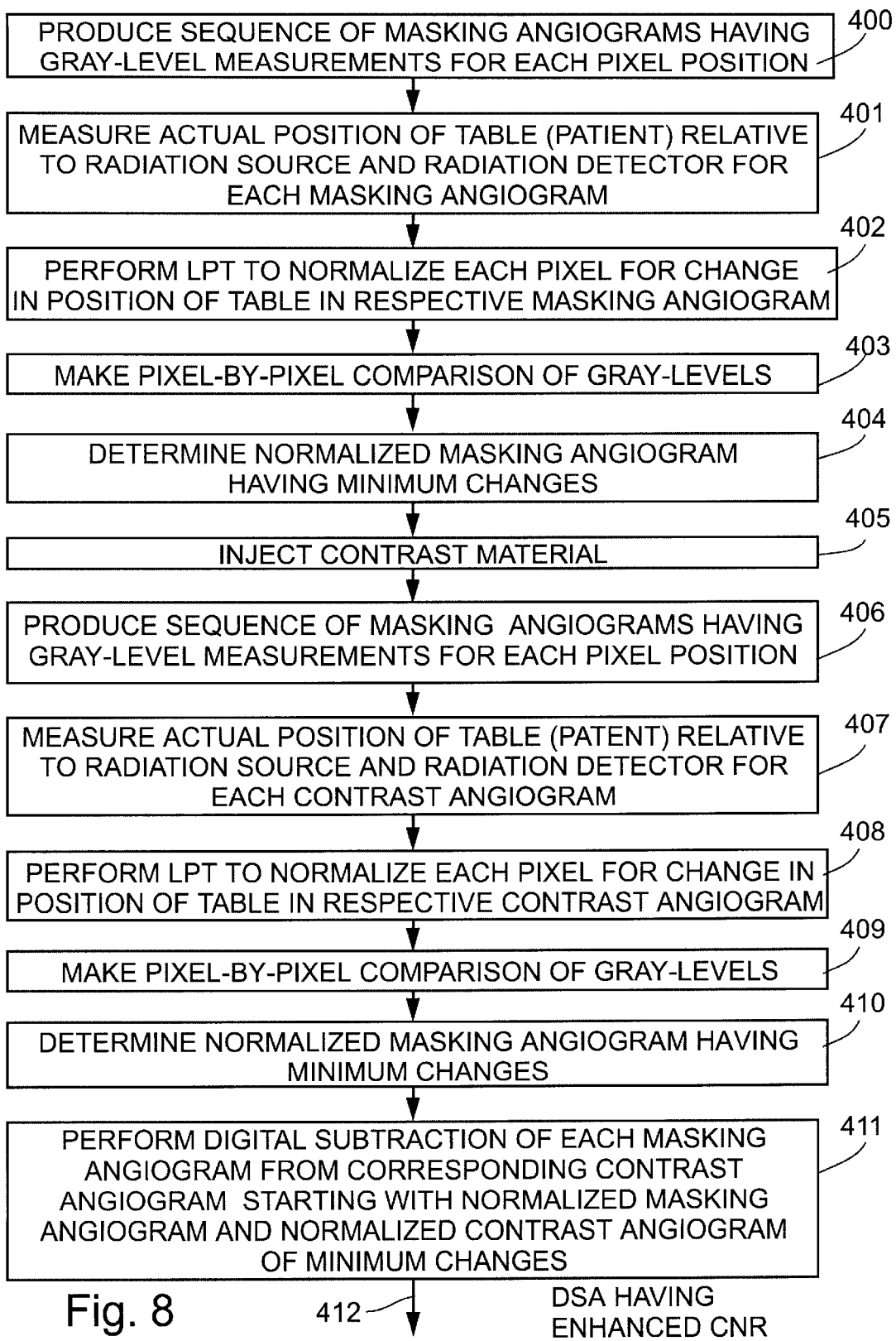
FIG. 8 is a flow chart illustrating the operation of the apparatus of FIG. 7.

The Embodiment of FIGS. 7 and 8

FIG. 7 is a block diagram illustrating a system similar to that of FIG. 1 but one permitting the patient's table 2 to be moved linearly continuously, or in stepped increments, with respect to the radiation source 5 and radiation detector 6 in order to examine a larger region of the patient's vascular system. In such a system, a linear positional transformation is performed to normalize each of the before-injection (masking) images, and the after-injection (contrast) images, with respect to the positional changes resulting from the relative movement between the patient and the radiation source and radiation detector between exposures.

The system illustrated in FIG. 7 includes means of the same components as that illustrated in FIG. 1, and therefore the same reference numerals have been used to identify corresponding components. The system of FIG. 7, however, also includes a Z-axis encoder 20 for driving table 2 along the Z-axis (i.e., the longitudinal axis of the patient's body 3), and a Z-axis encoder 22 for precisely measuring the movements of table 2 along the Z-axis. The illustrated apparatus further includes an X-axis motor 24 for driving the table 2 along the X-axis, e.g., transversely of the patient's body 3, and an X-axis encoder 26 for precisely measuring the movements of the table along that axis. It further includes a Y-axis motor 28 for rotating the gantry 4, and a Y-axis encoder 29 for precisely measuring the rotation.

It will thus be seen that when a patient 3 is on the table 2, and the table 2 is at a known referenced position with respect to the radiation source 5 and radiation detector 6, the position of each pixel element of the radiation detector 6 will be known; accordingly, by precisely tracking the movements of table 2 with respect to its referenced position, along both the Z-axis and X-axis, by means of the Z-axis encoder 22 and the X-axis encoder 26, respectively, the position of each pixel element may be normalized, by performing a Linear Positional Transformation (LPT) operation, for changes in the position of the table at the time an angiogram is produced.

The flow chart of FIG. 8 more particularly illustrates the operation of the system of FIG. 7 to normalize the masking and contrast angiograms with respect to changes in the position of the table 2 as measured by the two encoders 22 and 26, respectively.

Thus, as shown in the flow chart of FIG. 8, a sequence of masking angiograms is produced having gray-level measurements for each pixel position (block 400), while the relative position of the table 2 (and thereby of the patient 3) is measured, by the two encoders 22, 26, with respect to the radiation source 5 and radiation detector 6 for each masking angiogram (block 401).

An LPT (Linear Positional Transformation) operation is then performed to normalize each pixel in the masking angiogram for changes in position of the table for the respective masking angiogram (block 402). A pixel-by-pixel comparison is made of the gray-levels in each normalized masking angiogram (block 403) and a determination is then made, as described above, of the normalized masking angiogram having minimum changes with respect to its preceding normalized masking angiogram (block 404).

The contrast material is then injected (block 405) and the foregoing operations are repeated for preparing and processing a sequence of contrast angiograms (blocks 406–410).

The digital subtraction operation is performed with respect to the normalized masking angiograms and the normalized contrast angiograms to produce the DSA having enhanced CNR (block 411).

It will be appreciated that the system illustrated in FIG. 7 could also use reconstructed averaged masking angiograms, rather than a selected masking angiogram, for the minimum-change masking angiogram to be used as a reference in the digital subtraction process, where each masking angiogram is subtracted from its corresponding contrast angiogram, starting with the masking angiogram of minimum change as described above particularly with respect to the flow chart of FIG. 6. It will also be appreciated that the reconstructed masking angiograms could be reconstructed from more than two successive masking angiograms.

It will also be appreciated that the system illustrated in FIGS. 7 and 8 may also be used to produce a three-dimensional image in the same manner as described above, by rotating the gantry to a plurality of angular positions, producing a two-dimensional image at each angular position, and then reconstructing the plurality of two-dimensional images to a three-dimensional image.

It will be further appreciated that, in reconstructing the three-dimensional image, the large number of measured gray-levels (e.g., 128, 512, 1024) may be reduced to binary values "0" or "1", according to whether the magnitude of the radiation received by the respective detector element is above or below a predetermined threshold, as described for example in the above-cited application Ser. No. 09/946,168.

Therefore, while the invention has been described with respect to two preferred embodiments, it will be clearly understood that these are set forth merely for purposes of example, and that many other variations, modifications and applications of the invention may be made.

What is claimed is:

1. A method of angiographically imaging a portion of a patient's vascular system, comprising the steps:
   (i) producing a first sequence of masking images of said portion of the patient's vascular system;
   (ii) determining the masking image in said sequence having a minimum change over its immediately preceding masking image in said sequence;
   (iii) injecting a contrast material into the patient's vascular system;
   (iv) producing a corresponding sequence of contrast images of said portion of the patient's vascular system while containing said contrast material; and
   (v) subtracting from each contrast image of said sequence the corresponding masking image in the sequence, starting with said minimum change masking image, to thereby produce a difference image having an enhanced contrast-to-noise ratio (CNR);
   wherein in step (ii) a pixel-by-pixel comparison of the gray-level of the pixels in the respective masking image is made with the corresponding pixels in the preceding masking image of the sequence, and the masking image of the sequence having minimum changes over its immediately preceding masking image in the sequence is selected as said masking image of minimum change.

2. The method according to claim 1, wherein in said subtraction step, the respective contrast image is multiplied by a factor (k) of 1 to 3 before the corresponding masking image is subtracted therefrom.

3. The method according to claim 2, wherein said factor (k) is 1.8.

4. The method according to claim 1, wherein in step (v), there is subtracted from each contrast image of said contrast image sequence, the gray-levels of the corresponding masking image in the masking image sequence, starting with said minimum change masking image, to thereby produce a difference image having an enhanced contrast-to-noise ratio (CNR).

5. The method according to claim 1, wherein in step (v), there is subtracted from each contrast image of said contrast image sequence, the gray-levels of the corresponding masking image in the masking image sequence, averaged with the gray-levels of the next masking image in the masking image sequence, starting with said minimum change masking image, to thereby produce a difference image having an enhanced contrast-to-noise ratio (CNR).

6. A method of angiographically imaging a portion of a patient's vascular system, comprising the steps:
   (i) producing a first sequence of masking images of said portion of the patient's vascular system;
   (ii) determining the masking image in said sequence having a minimum change over its immediately preceding masking image in said sequence;
   (iii) injecting a contrast material into the patient's vascular system;

(iv) producing a corresponding sequence of contrast images of said portion of the patient's vascular system while containing said contrast material; and (v) subtracting from each contrast image of said sequence the corresponding masking image in the sequence, starting with said minimum change masking image, to thereby produce a difference image having an enhanced contrast-to-noise ratio (CNR); wherein:

said first sequence of masking images and said corresponding sequence of contrast images are produced by a radiation source and a radiation detector located on opposite sides of the patient;

relative linear movement is effected between the patient and said radiation source and radiation detector during said first and second image sequences;

and a linear positional transformation is performed to normalize each of said images with respect to said relative movement before the masking images are subtracted from the contrast images to produce said difference images having an enhanced CNR.

7. The method according to claim 6, wherein said linear positional transformation is performed by:

measuring the relative change in position of the patient with respect to said radiation source and radiation detector when producing said first sequence of masking images and said corresponding sequence of contrast images;

measuring the gray-level of each pixel position in each of said masking images and contrast images;

and modifying said pixel positions in each of the masking images and contrast images accordingly the measured relative change in position of the patient for the respective masking image and contrast image.

8. The method according to claim 6, wherein said patient is supported on a table movable along at least one horizontal axis with respect to said radiation source and radiation detector, and the movements of said table are measured and used for modifying said pixel positions in each of the measuring images and contrast images.

9. The method according to claim 6, wherein:

said radiation source and radiation detector are carried on a gantry which is rotated around said patient to a plurality of angular positions to produce a sequence of said masking images and said contrast images for each angular position;

a difference image having an enhanced CNR is produced for each of said angular positions;

and the difference images for said plurality of angular positions are reconstructed to produce a 3-D image of enhanced CNR.

10. Apparatus for producing angiographical images of a portion of a patient's vascular system, comprising:

a radiation source to be located at one side of the patient for radiating said portion of the patient's vascular system;

a radiation detector to be located at the opposite side of the patient for producing electrical outputs corresponding to the magnitude of the radiation received by the detector;

a computer for controlling said radiation source and for processing the outputs of said radiation detector to produce an image of said portion of the patient's vascular system;

and a display for displaying said produced image;

said computer controlling said radiation source and processing the outputs of said radiation detector such that:

before a contrast material is injected into the patient's vascular system and a sequence of masking images is produced of the portion of the patient's vascular system, a determination is made as to the masking image in said sequence having a minimum change over its immediately preceding masking image;

and after a contrast material is injected into the patient's vascular system and a corresponding sequence of contrast images is produced, from each contrast image the corresponding masking image in the sequence is subtracted, starting with the masking image determined to have a minimum change over its immediately preceding masking image, to thereby produce a difference image having an enhanced contrast-to-noise ratio (CNR) which is displayed in said display;

wherein said computer is programmed to determine the masking image of minimum change by making a pixel-by-pixel comparison of the gray-level of the pixels in the respective masking image with the corresponding pixels in the preceding masking image of the sequence, and selecting the masking image of the sequence having minimum changes over its immediately preceding masking image in the sequence.

11. The apparatus according to claim 10, wherein said computer is programmed to multiply the respective contrast image by a factor (k) of 1 to 3 before the corresponding masking image is subtracted therefrom.

12. The apparatus according to claim 11, wherein said factor (k) is 1.8.

13. The apparatus according to claim 10, wherein said computer is programmed to subtract from each contrast image of said contrast image sequence, the gray-levels of the corresponding masking image in the masking image sequence, starting with said minimum change masking image, to thereby produce a difference image having an enhanced contrast-to-noise ratio (CNR).

14. The apparatus according to claim 10, wherein said computer is programmed to subtract from each contrast image of said contrast image sequence, the gray-levels of the corresponding masking image in the masking image sequence, averaged with the gray-levels of the next masking image in the masking image sequences starting with said minimum change masking image, to thereby produce a difference image having an enhanced contrast-to-noise ratio (CNR).

15. The apparatus according to claim 10, wherein said apparatus effects relative linear movement between the patient and said radiation source and radiation detector; and said computer is programmed to perform a linear positional transformation to normalize each of said images with respect to said relative movement before the masking images are subtracted from the contrast images to produce said difference images having enhanced CNR.

16. The apparatus according to claim 15, wherein said computer is programmed to perform said linear positional transformation by;

measuring the relative change in position of the patient with respect to said radiation source and radiation detector in consecutive images;

measuring the gray-level of each pixel position in each of said masking images and contrast images;

and modifying said pixel positions in each of the masking images and contrast images accordingly to the measured change in the relative position of the patient for the respective masking image and contrast image.

17. The apparatus according to claim 10, wherein said apparatus includes a table for supporting the patient and movable along at least one horizontal axis with respect to said radiation source and radiation detector; and an encoder for measuring movements of said table.

18. The apparatus according to claim 10, wherein:

said radiation source and radiation detector are carried on a gantry which is rotated around said patient to a plurality of angular positions to produce a sequence of said masking images and said contrast images for each angular position;

said computer producing a difference image having an enhanced CNR for each of said angular positions and reconstructing said difference images for said plurality of angular positions to produce a 3-D image of enhanced CNR.

* * * * *